United States Patent [19]
Elson et al.

[11] Patent Number: 5,466,229
[45] Date of Patent: Nov. 14, 1995

[54] FLUID COLLECTION SYSTEM

[75] Inventors: Edward E. Elson, Anaheim; David H. Kuntz, Los Angeles, both of Calif.

[73] Assignee: Davstar, Inc., Costa Mesa, Calif.

[21] Appl. No.: 103,444

[22] Filed: Aug. 6, 1993

[51] Int. Cl.⁶ .................................................. A61M 1/00
[52] U.S. Cl. .................. 604/317; 604/257; 604/259; 604/260; 604/313; 604/319; 604/320; 604/321; 604/322; 604/323
[58] Field of Search .................... 417/4, 36–40; 137/587–588, 205; 604/317–324, 326, 30–31, 35, 905, 256–257, 259–260, 313, 315; 128/912; 13/319, 326, 357; 210/85, 86, 91, 97, 104, 252, 257.2, 258, 744

[56] References Cited

U.S. PATENT DOCUMENTS

| | | | |
|---|---|---|---|
| 2,784,717 | 3/1957 | Thompson | 604/319 |
| 4,111,204 | 9/1978 | Hessel | 604/320 |
| 4,275,732 | 6/1981 | Gereg | 604/320 |
| 4,396,016 | 8/1983 | Becker | 604/257 |
| 4,533,352 | 8/1985 | Van Beek et al. | 604/313 |
| 4,844,072 | 7/1989 | French et al. | 607/104 |
| 4,857,063 | 8/1989 | Glenn | 604/317 |
| 4,913,161 | 4/1990 | Villari et al. | 604/323 |
| 5,034,006 | 7/1991 | Hosoda et al. | 604/317 |

*Primary Examiner*—Randall L. Green
*Assistant Examiner*—P. Zuttarelli

[57] ABSTRACT

A fluid collection apparatus for the controlled collection of body fluids comprising a collection vessel housed in a carrier, a vacuum pump mounted in the carrier, and means for powering pump for continuous operation mounted therein. The collection vessel includes a valved exit port, and inlet port connected to a body mounted fluid collection apparatus, a vacuum control means, liquid level control means an tilt sensing means all operatively connected. Also described are a vented drainage valve assembly, and sound and odor absorbing components.

18 Claims, 9 Drawing Sheets

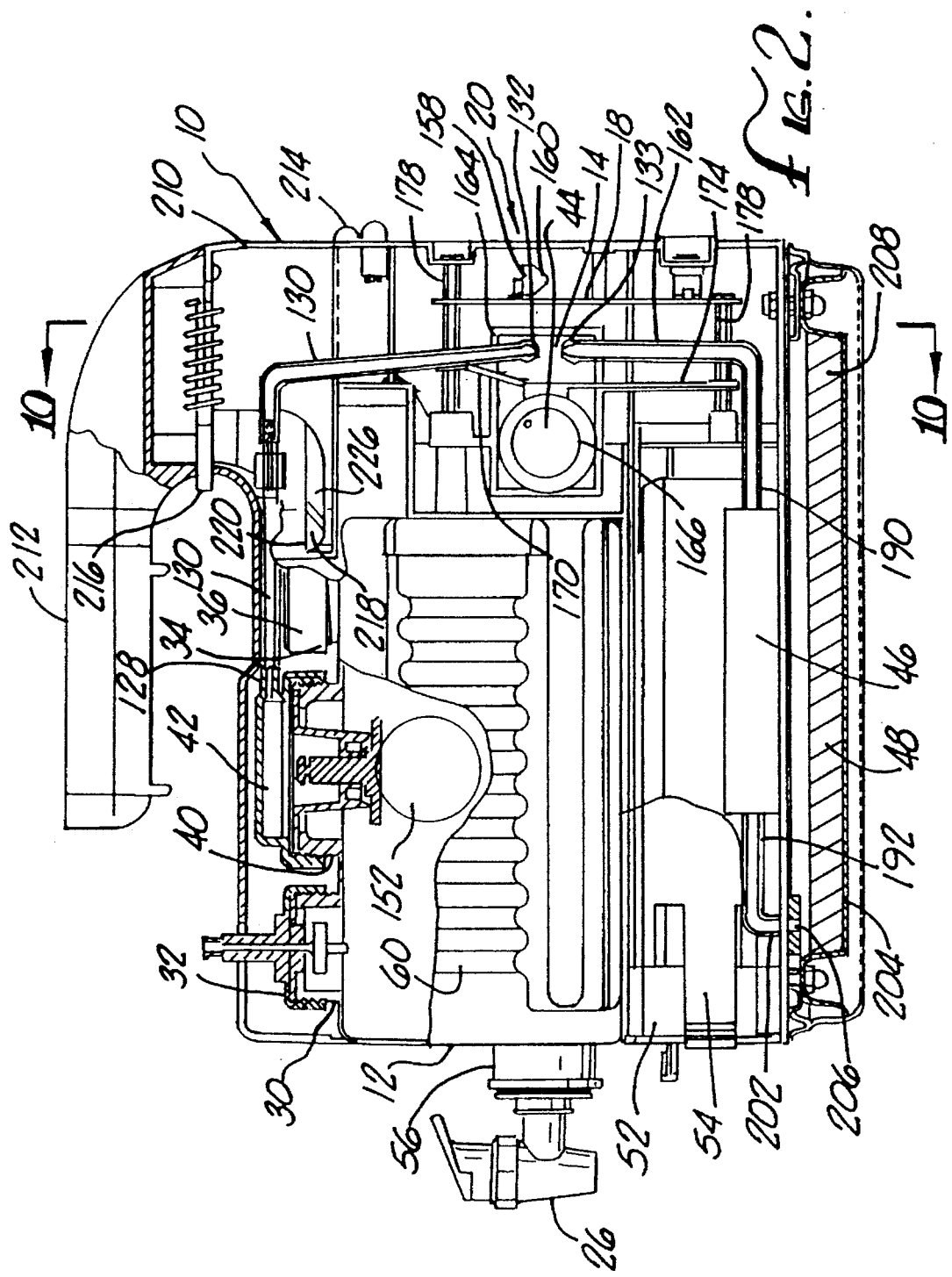

FLUID COLLECTION SYSTEM

BACKGROUND

The present invention relates to an improved system for collecting body fluids and unique components of the system. In particular, the system also includes a unique latching mechanism, vented valve, sound muffler, collection bottle, control mechanism, and pump and motor suspension system.

Urinary incontinence in patients, whether in hospitals, nursing homes, or at home, and irrespective of whether they are restricted to a wheelchair or bed or are ambulatory, presents a particular and continuing problem with respect to the care of such patients. Such incontinence is even more prevalent among the elderly. The problem is prevalent in both male and female patients but, for anatomical reasons, incontinence is a particular problem for women.

Methods used to manage these problems include frequent change of bedding, use of absorbent padding under the patients buttocks, perineal pads of various designs, or diapers. In order for these measures to be effective, the patient must be checked frequently and the moist padding must be changed promptly when damp. Diabetes Mellitus is a common ailment among these patients; the medical management of such patients may require checking tests of the urine several times daily. The use of pads and diapers impedes the collection of the necessary urine specimens for such testing. Such pads and diapers normally involve an absorbent core, typically a cellulose wadding or other hydroscopic material. These substances can absorb fluid only at a limited rate, and their total absorptive capacity is a function of their mass, typically about 10 grams of fluid per gram of material. Thus, the pad or diaper must be bulky in order to have an adequate capacity. Some pads and diapers incorporate hydroscopic gels to increase their absorptive capacity and minimize "wet-back", the release of previously absorbed fluid. As the gel absorbs fluid, it may form a barrier preventing penetration of fluid to more distal absorptive material. All pads and diapers have a limited and finite absorbency. Whenever the rate and volume of fluid passed exceeds this absorptive capacity, the excess leaks onto the clothing and bedding. Thus, such pads and diapers must be monitored frequently, replaced as soon as they become moist and before their capacity has been exceeded. Such monitoring must be carried out day and night at considerable inconvenience and expense.

Bacterial breakdown of urine within the moist padding may result in the release of ammonia which leads to skin irritation. Further bacterial activity may lead to skin breakdown and frank ulceration. Furthermore, bacterial multiplication within moist pads, diapers, clothing or bedding often produces noxious odors, unpleasant to patient, family members and care givers alike. Wet clothing and bedding must also be changed and this adds significantly to the time and expense associated with the care of incontinent patients. Added to the physical problems associated with the wet pads, diapers, clothing and bedding is the psychological and emotional cost to the patient and patient's family of the patient's regression to the child-like state of wearing pads or diapers. Replacement of urine soaked bulky pads and diapers involves handling pads and diapers, which is an unpleasant task, and which presents a risk of infection to the care giver. Changing of wet clothing and wet bedding also requires, generally, the services of more than one care giver with an attendant rise in the cost of providing care. Further, repeated replacement is also associated with the inconvenience and cost of storing a large number of pads, diapers, clothing and bedding to be ready for use and the costs associated with disposing of the pads and diapers and the added cost of cleaning the clothing and bedding. The disposal of large numbers of bulky, urine soaked pads and diapers creates an environmental and sanitary disposal problem of increasing concern.

Earlier attempts at dealing with the urinary incontinence problem include U.S. Pat. Nos. 3,349,768; 4,610,675; 4,713,065; 4,200,102; and 4,886,508. Foreign patents dealing with urinary incontinence include U.K. Patent No. 2,148,126A and French Patent No. 1,485,683.

A more recent method of dealing with urinary incontinence is disclosed in U.S. Pat. No. 4,747,166 to David H. Kuntz, entitled "Fluid Aspiration System for the Management of Urinary Incontinence." The aspiration system disclosed therein includes a vacuum pump and urine collection reservoir connected via a tube to an absorbent pad. The tube is connectable to the pad in one case through an opening and in another case by an opening engaging a coupling adapter. The pad disclosed therein had a series of highly absorbent cellulose tissue layers. The tissue layers are surrounded at the bottom by a thin impermeable layer and at the top by a permeable layer, the two layers joined at the lateral edges of the pad. In the preferred embodiment, a vacuum source connected to the system operates continuously, not only aspirating urine absorbed by the pad but, continuously, drawing air through the patient-pad interface, thus drying the pad and the contiguous skin surface. The Kuntz patent also discloses an embodiment which incorporates a fluid sensor in the pad which acts to turn off the pump if no fluid is present.

A similar approach was disclosed by Frank D. Martin in U.S. Pat. No. 4,631,061. The Martin aspiration system includes a vacuum pump and urine collection reservoir connected via a tube to a collection vessel formed from a non-absorbent, liquid impervious material. The Martin collection vessel or tube further includes a sensor which detects the presence of urine. The sensor is connected to the pump on-off switch so the vacuum pump is automatically turned off if no urine is present.

It has been found that devices such as shown in Kuntz or Martin have several deficiencies regarding the ease of operation, the procedures for connecting and emptying the collection container and techniques for removing a fresh urine sample without opening the system. Further, it has been demonstrated that urine will travel posteriorly in or on a collection pad or vessel in a supine or reclining patient and that sensors in the outflow of the pad or collection means may be bypassed with the result that the patient, the patient's clothing and the patient's bedding may become wet. Additionally, the time delay in establishing the level of vacuum required to aspirate the urine from the collection means may be significant if the vacuum pump is in the off mode noted in the Kuntz and Martin devices. Such systems where urine is aspirated through tubing into a reservoir connected to a vacuum pump present certain design problems: For example, emptying such a reservoir at a reasonable rate requires special design of the drainage port to permit rapid inflow of air to offset pump action. Means must be incorporated to prevent accidental backflow of urine from the reservoir to the pad or collection vessel. Aspiration of fluid from the reservoir into the pump, thereby damaging or disabling it, must be prevented. Since the reservoir may contain infected urine, some means must be provided to prevent discharge into the room of hazardous fluids by aerosolization. The mechanism must be protected from damage due to tipping or overfilling of the reservoir. As urine aspiration requires a constant source of vacuum, means to indicate kinked tubing or other blockage of the system preventing flow should be provided. In the event of any of these occurrences, means to alert the patient or care giver should be provided. Parts of the system more likely to require servicing or replacement, (for example, the tubing, filers or reservoir) must be designed so that servicing or replacement may be done with ease. The system should contain means for securing a fresh sample of urine for monitoring diabetes. It must include means for operation when the patient is out of bed, in a wheel chair, or is ambulatory. This type of operation obviously must be by battery; so, means must be included to indicate the type of power in use, and the status of the battery. Since battery life is generally proportional to battery size and weight, the design must incorporate sufficient power without requiring overly frequent recharging. These means include a pump with low current draw and an integral battery recharging system. Since passage of urine is an intermittent function, means should be provided to modify pump performance to the changing requirements of the system.

All of these requirements should be provided by a device which is sturdy, yet small and light enough to be carried in one hand and easily adaptable to be attached to a bed or wheel chair. The controls and indicators must be sufficiently simple so the system may be safely and efficiently operated by relatively unsophisticated persons.

Thus, there is a need for a fluid collection device capable of continuous operation for collecting urine from incontinent patients that is safe to use, easy to operate, convenient to set up or empty, allows easy replacement of disposable elements such as tubing and the urine collection reservoir, has a minimized risk of spilling, overflowing or otherwise contaminating the vacuum pump or surrounding area, and offers the ability to obtain fresh urine samples without disconnection the system, removing the collection pad or shutting off the pump.

SUMMARY

These needs are met by the present invention which is a collection system comprising a fluid collection container and a vacuum pump, along with various control devices, attached to a carrier. The collection system is connected to a fluid collection pad or appliance worn by an incontinent individual. The container has several closable ports in upper surfaces for the insertion and removal of an inlet connector having a one way valve, a control connector having a liquid level sensor, a vacuum sensor and/or a pump shut-off valve, and a vacuum connector including a bacterial filter associated therewith. Located in a surface is a valved drainage port, which may also be vented, the vent being opened only during the drainage procedure. In a preferred embodiment, the vented drainage part is located in a wall of the container, at or near the bottom of the container. The vacuum pump outlet includes an odor absorbing material and is muffled to decrease or eliminate noises generated by operation of the pump. Operatively connected to the pump is a tilt switch. Activation of the switch by tilting the carrier in any direction by an amount greater than a preset angle will cause the pump to automatically shut off. Located along the tube connecting the container to the pad or appliance worn by the incontinent person is a sampling chamber through which freshly collected urine myst pass before entering the container. Vibration and noise is further reduced by at least partially encapsulating the pump and motor in an elastomeric holder and suspending the pump and motor within the system.

In a preferred embodiment the vacuum port is centrally located in the center of the upper surface of the container to minimize aspiration of fluid into the vacuum pump.

DRAWINGS

These and other features, aspects and advantages of the present invention will become better understood with reference to the following description, appended claims, and accompanying drawings, where:

FIG. 2 is a partially cutaway side view of the system of FIG. 1 showing the major internal components.

FIG. 7 is an enlarged cross-sectional view of the inlet port and inlet connector taken along line 4—4 of FIG. 4a.

FIG. 8 is an enlarged cross-sectional view of the control port, control connector and a first embodiment of a liquid level sensor taken along line 4—4 of FIG. 4a.

FIG. 9b is an enlarged cross-sectional view of the vacuum import and vacuum connection in the open position taken along line 4—4 of FIG. 4a.

DESCRIPTION

Figure 1:
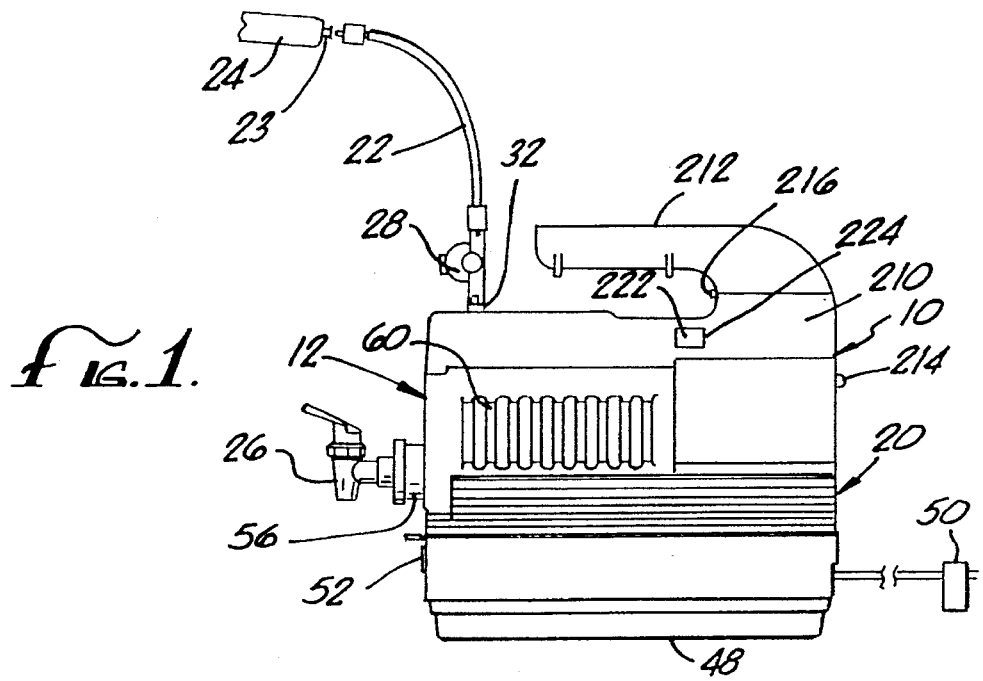
FIG. 1 is a side view of the body fluid collection system embodying features of the invention showing the fluid collection container attached to a carrier.
Figure 3:
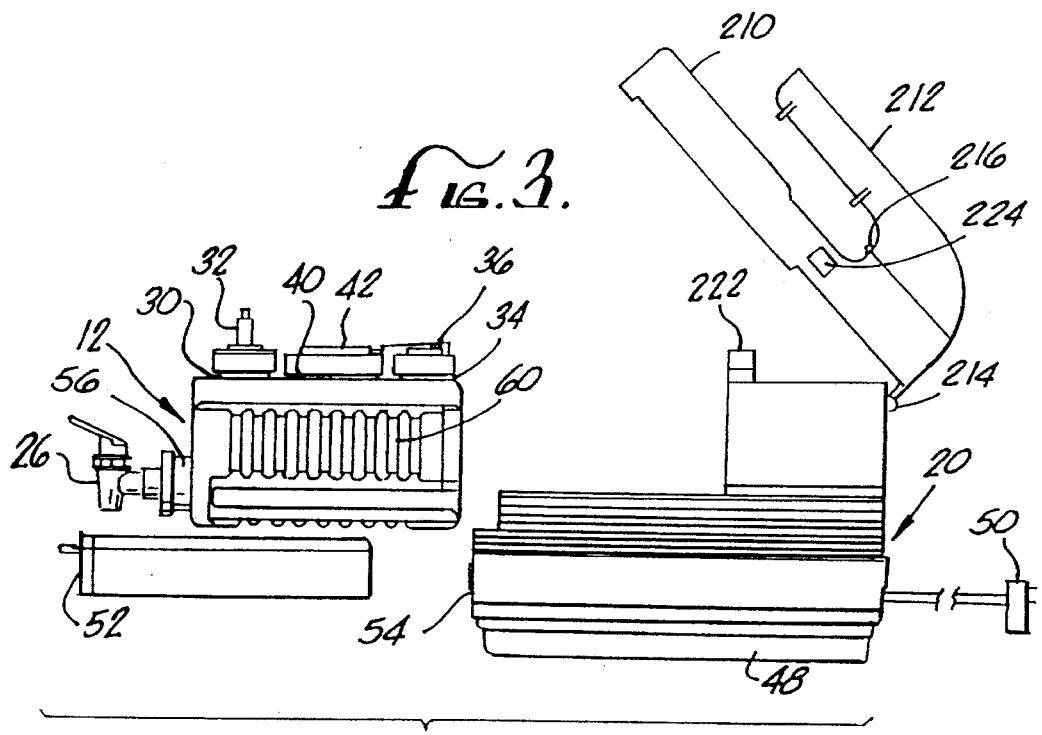
FIG. 3 is an exploded side view of the collection system of FIG. 1 showing the removable and movable components.

FIG. 1 shows the system assembled, FIG. 2 shows an exploded view of removable components and FIG. 3 is a cross-section view showing the location of the major components, both fixed and movable.

FIGS. 1, 2 and 3 show a preferred version of the body fluid collection system 10 incorporating features of the invention. The main components of the fluid collection system are a removable container 12, a vacuum pump 14, a power source (batteries or standard AC wall outlet connection, an electrical control module 18 and a frame 20 to which each of the main components are mounted. Connected to the container 12 is a tube 22 which is in turn connected to a fluid collection pad 24 placed over the urethra by an incontinent individual. U.S. Pat. No. 4,747,166 to Kuntz, which shows a suitable body mountable pad, is incorporated by reference.

Figure 4A:
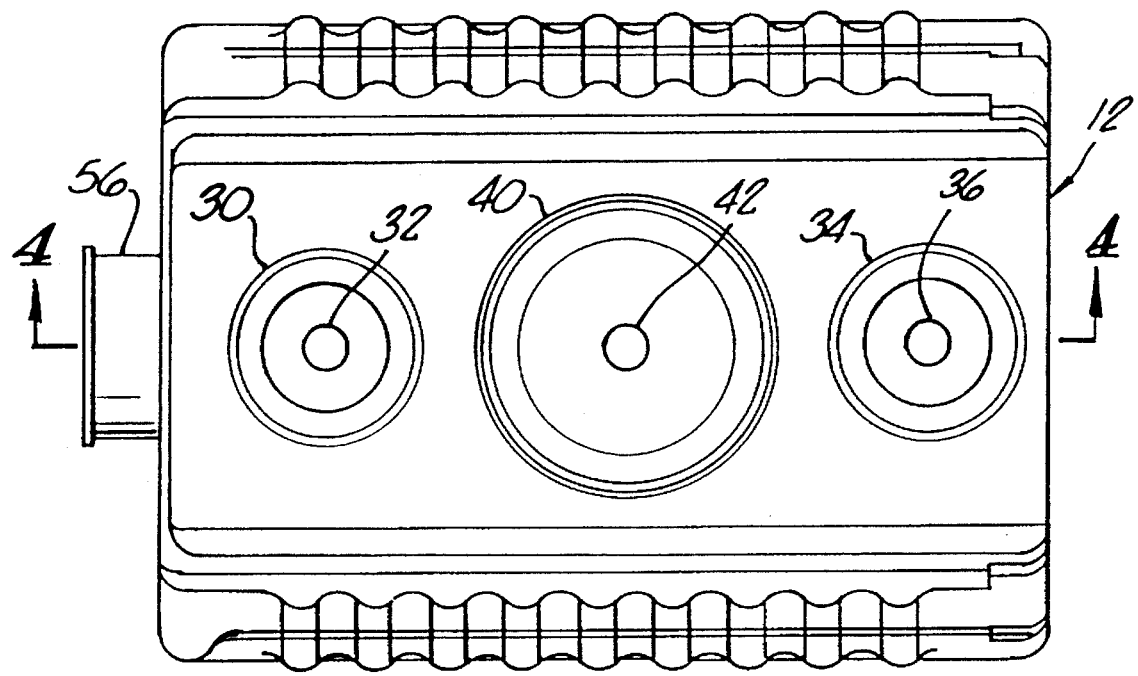
FIG. 4a is a top view of the container of the fluid collection system of FIG. 1.
Figure 4B:
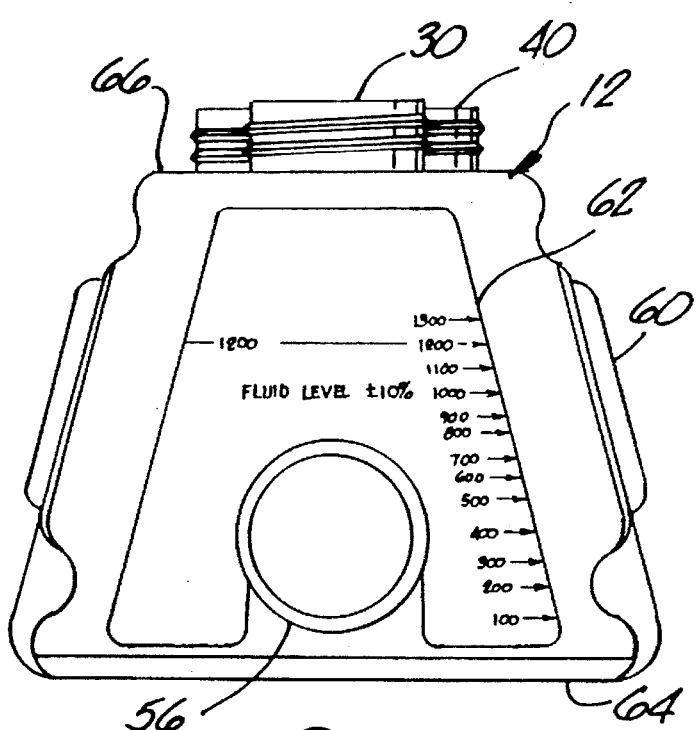
FIG. 4b is an end view of the container of the fluid collection system of FIG. 1 with the connectors removed.
Figure 4C:
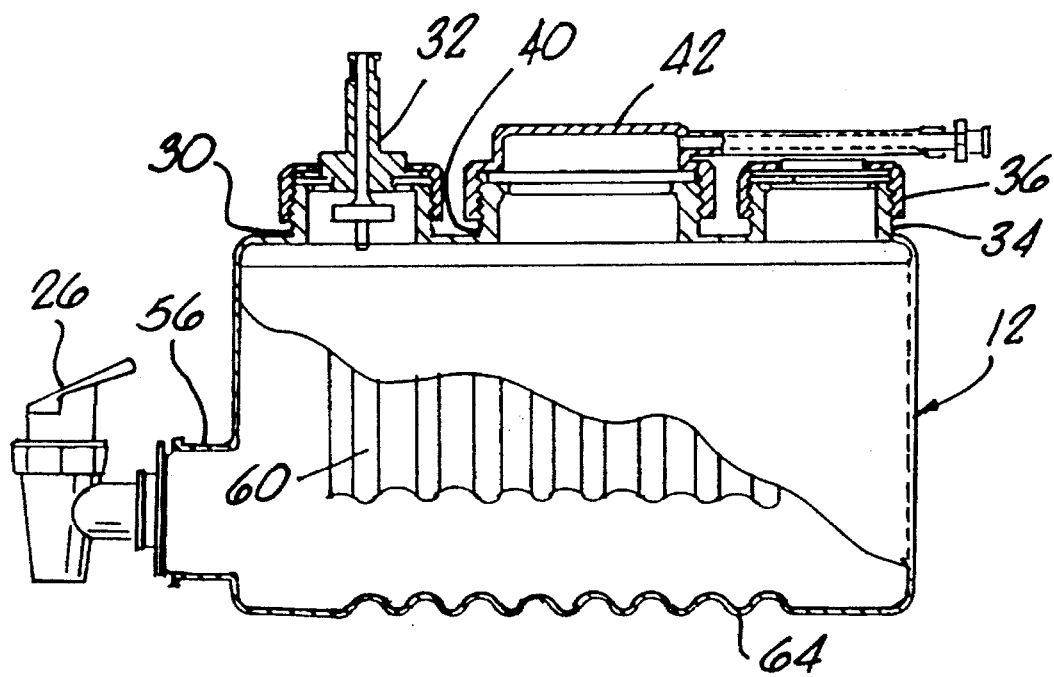
FIG. 4c is a partial cutaway view of the container taken along line 4—4 of FIG. 4a with connectors attached to the top ports and a valve attached to the lower port.

FIGS. 4a, 4b and 4c show the removable collection container 12. FIGS. 5–11 show various embodiments of subassemblies, the subassemblies being enlarged for clarity. In particular, FIGS. 5–11 show an outlet valve 26, sampling chamber 28, the inlet port 30 and inlet connector 32, the control port 34, control connector 36 and liquid level sensor 38, the vacuum port 40 and vacuum connector 42, the motor 44 and the vacuum pump 14, and the exhaust muffler 46.

The embodiment shown in FIGS. 1–3 includes a frame 20 which surrounds and encloses each of the components of the system. Permanently mounted to an inner end wall of the frame 20 is the electrical control module 18.

Figure 12:
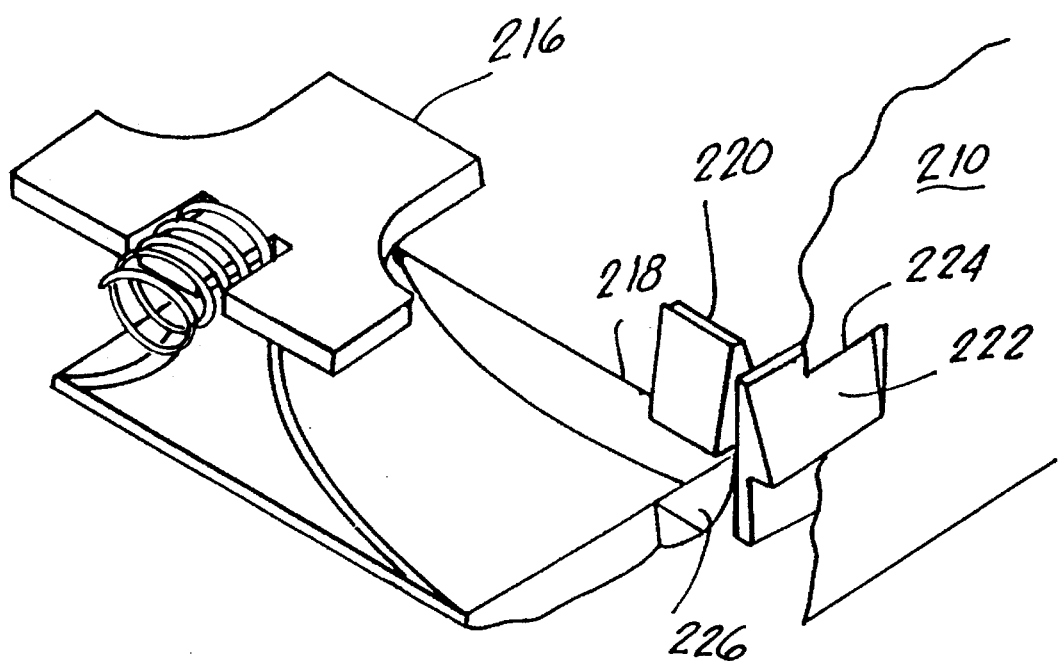
FIG. 12 is an enlarged perspective cutaway view showing the locking mechanism of FIG. 3.

Attached to the frame 20 is a cover 210 which serves the dual purpose of securing the removable container 12 in the frame 20 and providing a handle 212 to facilitate carrying the system 10. In the embodiment shown, the cover 210 is movably secured to the frame by a hinge 214 located on frame 20. In its open position (FIG. 3), the cover swings up to allow the container 12 to be removed. In its closed position (FIGS. 1 and 2) the cover 210 prevents accidental removal of the container. Also, the closed cover 210 protects the vacuum line 130 from being crimped and connectors 32, 36 and 42 from being damaged. To prevent accidental opening, the cover 210 has two discrete latching mechanisms which requires two hand operation to open. The latching mechanism, best shown in FIG. 12, includes a spring loaded trigger 216, which extends partially through the handle 212, when cover 210 is in the colsed position, at least one finger 218, integral with the finger 216 sits under an etension 220 on an inner surface of the frame 20. Additionally, also mounted on the frame 20 is at least one locking tab 222 which, when the cover 210 is in its closed position, sets into and is held by an indent or opening 224 on the cover 210. On the outer surface of the finger is a raised angular portion 226 which presses on an inner surface of the locking tab 222, forcing the tab 222 into the opening 224 if the trigger 216 is not depressed at the same time. To swing the cover 210 to its open position and gain access to the container 12, the trigger 216 and tab or tabs 222 must be simultaneously depressed. Pressing the trigger 216 pulls the finger 218 out of contact with the extension 220 and moves the raised angular portion from behind the locking tab 222; pressing the locking tab 222 extracts the tab 222 from the opening 224. If the trigger 216 and the tab 222 are not both removed from interaction with the cooperating extension 220 and opening 224, the cover 210 will not swing to its open position.

While a single locking structure, either the trigger 216 and extension 220 or the tab 222 and opening 224 may be adequate to keep the cover 210 attached, the added security of the double locking structure is preferred. Further, different locking mechanisms or a reversal of the parts may be used to maintain the cover 210 in a closed position. Also, while the cover 210 is shown to be hinged at one end of the frame 20, it may be hinged at various locations on the frame 20. Alternatively, the cover may be totally removable to gain access to the container 12 and other components under the cover 210. In such an instance, the cover can be held on by interlocking pieces on the frame and cover screws or bolts, straps or similar mounting means.

The frame 20 is preferably fabricated from a plastic material molded into a structure suitable for enclosing, mounting and protecting each of the components of the system. However, the frame 20 may alternatively be fabricated as an open skeleton-like structure designed to carry and protect but not necessarily enclose the components. While materials other than plastics may be used to form the frame, the preferred materials are structural plastics or reinforced plastics which may be molded into the desired shape such as polypropylene, reinforced nylon, polyesters, polycarbonate, polycarbonate blends or other tough, high impact polymers.

The vacuum pump 14 and motor 44 are suspended within the frame 20 in close proximity to the control module 18. The system 10 can be powered by being plugged directly into a wall outlet using a detachable wall mounter power supply 50 or by battery 52 inserted in a tray 54 in the bottom of the system 10. Preferably, the battery 52 is rechargeable in which case the wall mounted power supply 50, shown in FIGS. 1 and 2, is used to recharge the batteries 52 through an AC to DC power converter and charger (not shown) included within the frame 20, and, for example, mounted on the control module 18. To allow access to the pump 14, control module 18, and the power source 16 for maintenance and repair, the frame can also have removable or openable panels covering these components.

FIGS. 4a–4c show a version of the container 12. The container 12 is constructed to be easily removed from the system and disconnected from components such as the inlet connector 30, control connector 34 and liquid level sensor 36, the vacuum connector 40 and the outlet valve 26 which may be reused or discarded when it is desired to use a new container or the system is cleaned for use by a new patient. In particular, the container 12 has three openings or ports 30, 34, and 40 in the top surface and a fourth port 56 in a lower wall of the container 12. As shown in FIGS. 4a and 4b, the four openings can each have a raised threaded portion surrounding the opening for attachment of caps with mating threads, the attached caps being shown in FIGS. 5, 6, and 7. Additionally, the container 12 can have a handle (not shown) molded into the unit for ease in handling. However, the embodiment shown has the handle 212 being part of the cover 210 on the frame 20 rather than on the bottle. While the Figures show threaded fittings, the container 12 can be formed with various different attachment structures, including quick release snap on fittings or bayonet type connectors, the criteria being that removable components can be easily attached and removed and, once connected, form a vacuum tight seal. Alternatively, the connectors may provide for permanent attachment of components such as the valve 26 shown in FIG. 4c which is heat sealed, glued or pressure fitted onto the vessel.

In the embodiment shown in FIGS. 1–4, the container 12 is a non-collapsible bottle of fixed dimensions molded from a readily formable but stiff plastic such as polyethylene, polypropylene or PETG. As shown in FIG. 4B, a preferred volume capacity is about 1200 cc which constitutes an average normal urine output in a 24 hour period.

Other features which may be included in the bottle are ribbed sides 60 to prevent the bottle from collapsing under high vacuum and volume markings 62 to indicate the bottle contents. The container 12 can be nested in the frame 20 or may be located at a distance from the vacuum source. To accommodate remote placement, the container 12, as best shown in FIG. 4b, can be formed with a base 64 which is wider than the top surface 66. This reduces the possibility that the container 12 will tip over during use.

While the drawings show a non-collapsible container 12, it is also possible to use a container which is flexible and collapsible. For example, a bag formed from flexible sheet material, such as polyethylene, vinyl or mylar-saran-polyethylene blends, can be adapted to fit in a frame and receive the removable components. The bag can be collapsed under vacuum as long as the vacuum is transmittable to the pad and the bag is adapted to receive fluid being collected without obstruction of the fluid flow and the bag expands as it is filled. For example, bags currently used for gravity collection of urine through an indwelling urinary catheter can be adapted to be used in the fluid collection system 10.

FIGS. 1–4 show the container 12 having a conventional spigot valve 26 such as can be applied to containers to allow draining of its liquid contents. For example, the valve shown has a spring loaded lever handle which, in its depressed or activated mode allows fluid to drain. Other usable valves employ various means to slide or rotate a core stem to unblock the drainage port on the container.

It is desirable that the container have venting means incorporated therein so that air can be allowed to enter the container as liquid is removed from it. However, it is preferred that flow of air in and out of the container 12 is restricted to prevent bacteria from entering or leaving the container. This can be accomplished by placing an openable vent in the wall of the container or one of the connectors mounted to the top of the container. The container 12 can then be vented to allow air in while the valve 26 is opened.

Another approach is to allow air to enter through the valve countercurrent to the liquid draining from the container. This can cause a gurgling and splashing of the liquid exiting the valve and can also cause a bubbling and foaming of the liquid remaining in the vessel. If the liquid is viscous, and a vent isn't present, flow of the fluid through the valve can be interrupted or prevented by a vacuum applied or created in the container.

Gurgling and splashing of the liquid exiting the valve can be hazardous to personnel in the area if the fluid is hazardous, toxic, corrosive, or contains infectious substances such as bacteria or viruses, as the gurgling and splashing can spray the liquid on personnel or vaporize some of the fluid, contaminating the ambient air which surrounds or is breathed by personnel.

Figure 5A:
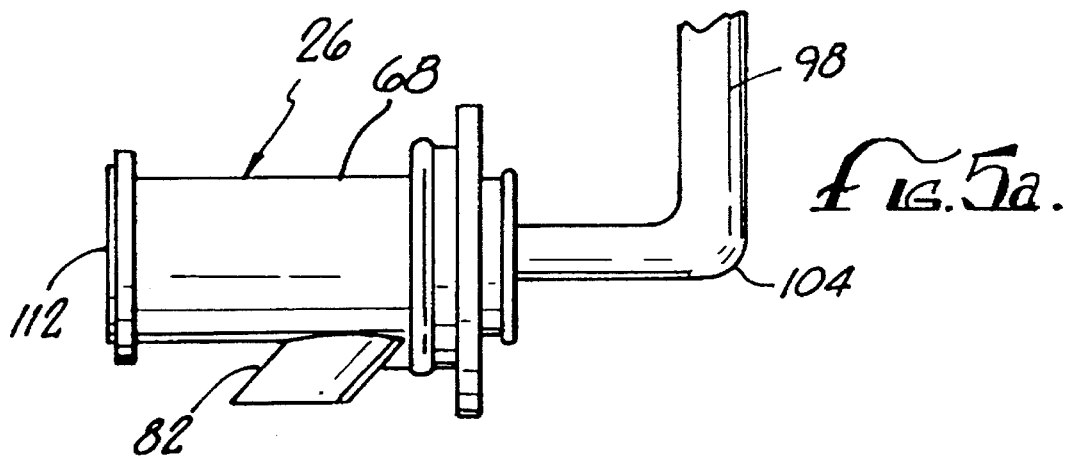
FIG. 5a is a side view of a second embodiment of a valve for attachment to the lower hole in the container, the valve being shown in its closed configuration.
Figure 5B:
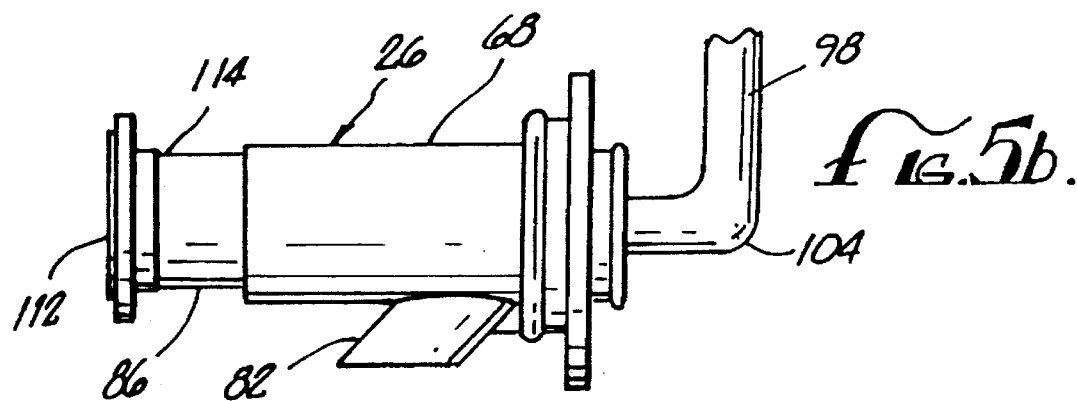
FIG. 5b is a view of the valve of FIG. 5a in its open configuration.
Figure 5C:
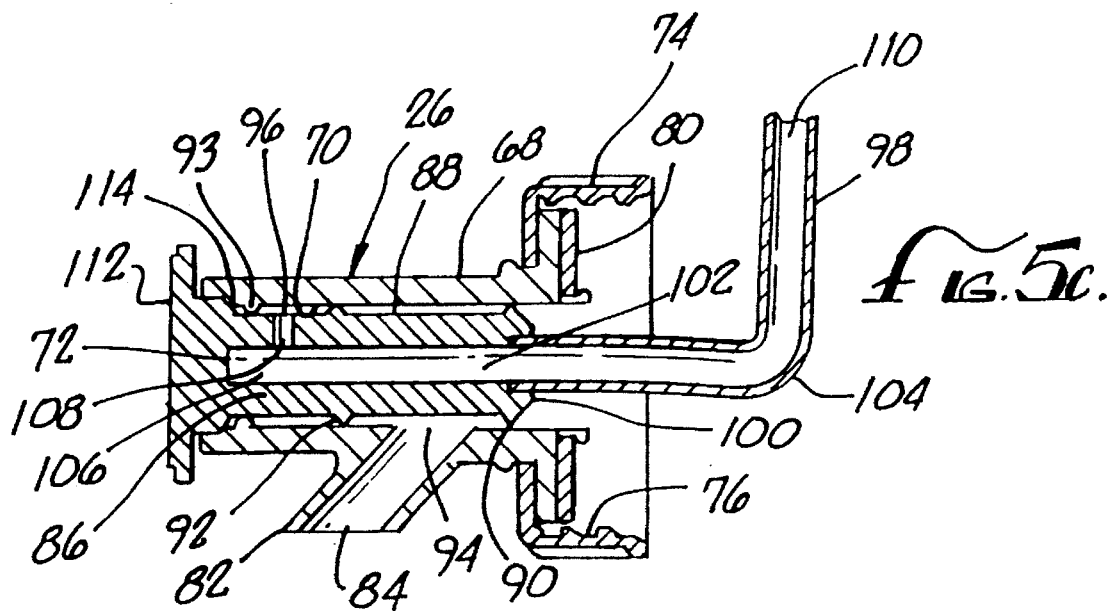
FIG. 5c is a longitudinal cross-sectional view of the valve of FIG. 5a in its closed configuration.

FIGS. 5a–5c show an outlet valve 26 particularly useful for draining fluid from a container having its contents under vacuum. In order to drain liquid from the container 12 without causing splashing or bubbling of the liquid as air rushes in the open valve 26 to fill the vacuum, it is preferred that means in the valve be made available to vent the container 12 during the drainage procedure. It is further preferred that the air be vented to the space above the liquid in the container 12 instead of bubbling through the liquid which can vaporize some of the liquid, carrying vapor and bacteria into the vacuum pump 14. It is additionally preferred that the vacuum pump 14 not be shut off during drainage so that at least some vacuum is continuously applied to the fluid collection pad 24.

The outlet valve 26, shown in the FIGS. 5a–5c, has a tubular outer shell 68 with a smooth inner surface 70 and a lumen 72 extending its full length. On one end of the tubular outer shell 68, as shown in FIG. 5c, is a freely rotating threaded connector 74, the threads 76 being fabricated to mate with the matching threads which can be located on the outlet port 56. When the connector 74 is threaded onto the outlet port 56, gasket 80 renders the connection leak proof. Depending from the shell 68 is a hollow spout 82, the lumen 84 of which is connected to the lumen 72 of the tubular outer shell 68. Positioned in the center of the shell 68 and extending the full length of the shell 68 is a hollow piston 86. On the outer surface 88 of the piston 86 is a first raised ridge or seal 90 and a second raised ridge 92. On the inner surface 70 of the shell 68 there is also located a third ridge or seal 93. The seals 90, 92 are sized so that the piston 86 can slide through the lumen 72 of the shell 68 while, at the same time, the clearance between the seals 90, 92 and the shell inner surface 70 is liquid tight. The first and second seals 90, 92 are located so that the first seal 90 is on one side of the internal opening 94 of the spout lumen 84 and the second seal 92 is spaced from the first seal 90 and on the opposite side of the spout lumen internal opening 94 when the valve 26 is in its closed position (FIGS. 5a, 5c), i.e. the two seals 90, 92 isolate the spout lumen 84 from the contents of the container 12 on one side and the second seal 92 and the third seal 94 isolates the vent opening 96 (described below) from the spout and the contents of the container 12. While FIG. 5c shows the first and second seal 90, 92 on the piston and the third seal 93 on the inner surface 70 of the valve 68, the locations can be reversed or the seals can all be located on the piston outer surface 78 or the valve inner surface 70.

When the valve 68 is attached to the container 12, in order to prevent air entering the open valve 68 from bubbling through the urine in the container 12, a vent tube 98 is preferably attached to the piston interior end 100 of the piston lumen 102. The vent tube 98 which extends a distance from the end of the piston interior end 100 and then has a bend 104 of about 90° so that the vent tube opening 110 extends above the highest level expected for urine in the container. Near the opposite, exterior end 106 of the piston lumen 102 is a channel 108 at an angle, preferably 90°, to the piston lumen 102 such that the channel 108 connects the piston lumen 102 with a vent opening 96 on the piston outer surface 88, resulting in a continuous open path from the vent tube interior end 110 through the piston interior end 100 and lumen 102 to the vent opening 96 near the piston exterior end 106.

On the piston exterior end 106 is a knob 112 which can be grasped and pulled to slide the piston 86 along the shell lumen 72 when drainage of the container 12 is desired. Also, the piston exterior end 106 is enlarged at a point between the knob 112 and the vent opening 96 to form a vent seal 114 which causes the piston outer surface 88 to form a fluid seal with the shell interior surface 70.

When the piston 86 is in its closed position (FIGS. 5a, 5c) the vent seal 114 and third seal 93 isolates the channel 108 and prevents ambient air from entering the vent opening 96 and thus the vacuum is maintained in the container 12. When the piston 86 is in its open position (FIG. 5b) the vent seal 114 is removed from contact with the shell inner surface 70 and the vent opening 96 is moved past the third seal 93, allowing ambient air to enter the vent tube 98 and the container 12. At the same time, the first seal 90 is withdrawn past the internal opening of the spout 94 and liquid is allowed to flow through the shell lumen 72 and through the spout 82.

The valve shell 68 and the piston 86 can be formed from polymeric materials such as polypropylene, polycarbonate, teflon, or polyvinylchloride (PVCP). Alternatively, the shell 68 and/or the piston 86 can be formed from metals such as aluminum, stainless steel, or plated brass. While FIG. 5c shows the seals 90, 92, 93 as an integral part of the piston and/or the shell, they can also be applied as separate components to the piston or shell. For example, the ridges or seals 90, 92, 93 can be separate components, such as an elastomeric or polymeric sealing ring, applied to the outer surface 88 of the piston 86 or the inner surface 70 of the shell 68 rather than being formed directly on the surface of the piston 88 or, alternatively, on the inner surface wall 70 of the shell 68. As a further alternate construction, one or two of the seals 90, 92, 93 can be located on the piston 86 and the other seal can be on the shell inner surface 70. This placement requires the formation of a groove in the piston or shell surface to retain the seal 90, 92, 93 in its desired position.

The valve 26 described above includes a threaded fitting 74 for mounting the valve to a matching threaded opening on the vessel. However, other mounting means or interfitting connectors, such as expandable or contracting connectors, levered connectors snap fittings, or other attachment means, commonly referred to as quick release connectors, may be used. Additionally, the valve can be permanently attached to the vessel.

Figure 6:
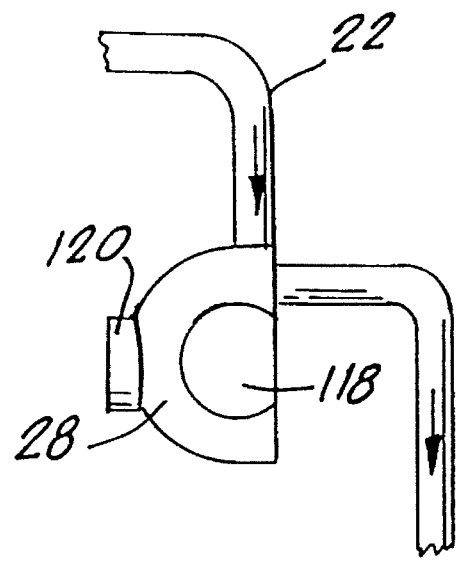
FIG. 6 is an enlarged side view of a sampling chamber mounted in the inlet tube.

The drain tube 22, usually constructed of a flexible rubber, or elastomeric or polymeric material, such as polyethylene, polyester or polyurethane which will not collapse under vacuum, connects the pad 24 with the container 12. The tube 22 is attached to an inlet fitting 116 on the top of the inlet connector 32 which is, in turn, attached to the inlet port 30. Located along the drain tubing 22 above the inlet connector 32 or between the end of the drain tubing 22 and the inlet connector 32 is a sampling chamber 28. FIG. 6 shows one version of the sampling chamber 28 which allows a sample to be removed or gives a visible indication that fluid is flowing. Liquid drawn from the pad 24 by the vacuum in the system 10 flows through the drain tube 22 into the container 12. The sampling chamber 28 allows the flow of fluid to be observed and, if desired, a fresh sample of the fluid to be remove from the system without breaking the integrity of the system 10. Various different techniques can be used to remove a sample. For example, the sample chamber 28, such as shown in FIG. 6, can include a pierceable and resealable septum 118 which can be repeatedly punctured by a hypodermic needle. Alternatively, the sampling chamber 28 can include a valved opening 120 which is temporarily opened by the attachment of a suitable receptacle such as a urine collection tube. Examples of suitable urine collection tubes are shown in U.S. Pat. Nos. 3,814,522 to Clark, 4,865,812 to Kuntz et. al. and 5,030,421 to Muller.

Figure 7:
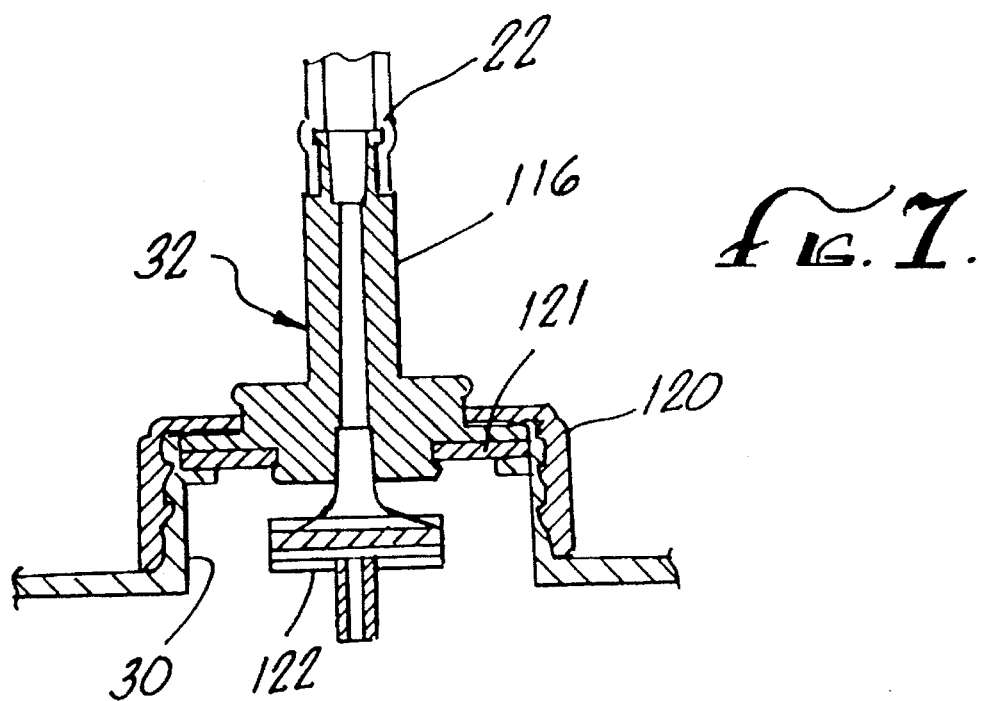

FIG. 7 is an enlarged drawing showing the inlet port 30 and inlet connector 32. The inlet port 30 threaded onto the inlet connector 32 which includes means to mate with the inlet port 30 in a vacuum tight manner, such as a threaded cap 120 and sealing gasket 121, an inlet fitting 116 for attachment of the drain tube 22 or outlet of the sampling chamber 28, and a one way valve 122 suspended below the cap 120. Liquid flowing along the drain tube 22 flows through the one way valve 122 into the container 12. The one way valve 122 prevents the liquid in the container 12 from reentering the drain tube 22 if the container 12 becomes overfilled or the system 10 is tilted so the valve 122 becomes emersed in the collected liquid.

Figure 8:
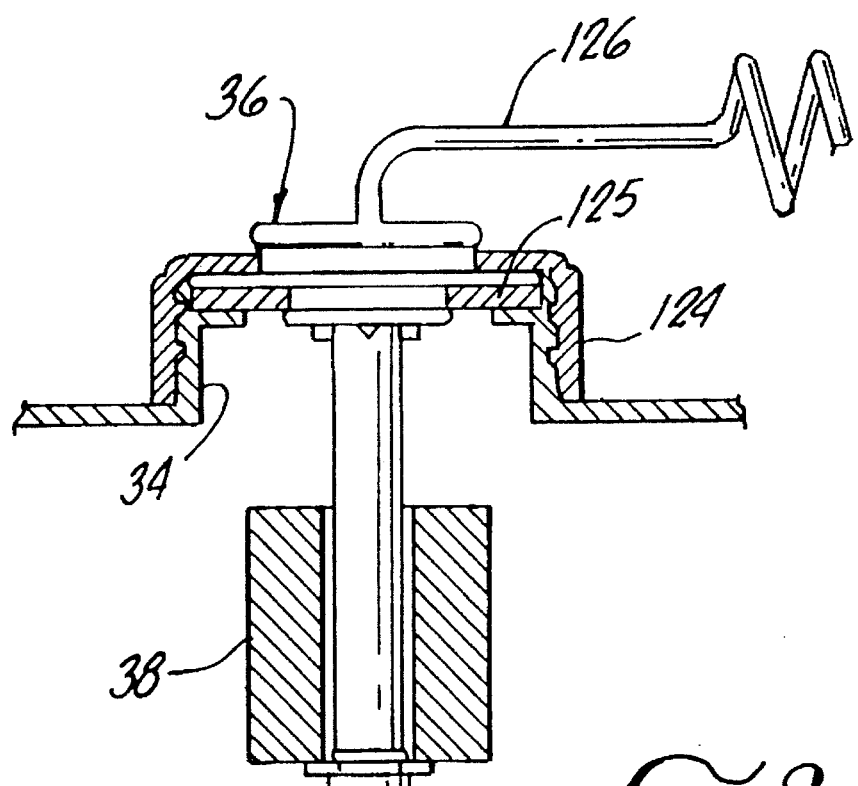

FIG. 8 is an enlarged cutaway drawing showing the control port 34. Removably attached to the control port 34 is a control connector 36 which includes means to mate with the inlet port 34 in a vacuum tight manner, such as a threaded control cap 124 and gasket 125, a liquid level sensor 38 mounted below the cap 124 and signal transmitting means 126 for transmission of the signal from the liquid level sensor 38 to the control module 18. The sensor indicates fluid level and shuts off the motor if the level is too high. Various different liquid level sensors may be used such as a float which is raised as the quantity of liquid increases, electrically sensors which respond to contact by the liquid filling the container, optical switches which sense the proximity or contact by the fluid, or magnetic or ultrasonic proximity switches. The signal transmission means 126 can be selected from a broad range of mechanisms which are capable of transmitting a signal from a first point to a second point such as electrical wires, fiber optic cables, hydraulics or mechanical linkages. Alternatively, the liquid level sensor can be eliminated, the control port 34 can be closed by a blank cap and the contents can be visually monitored.

Figure 9A:
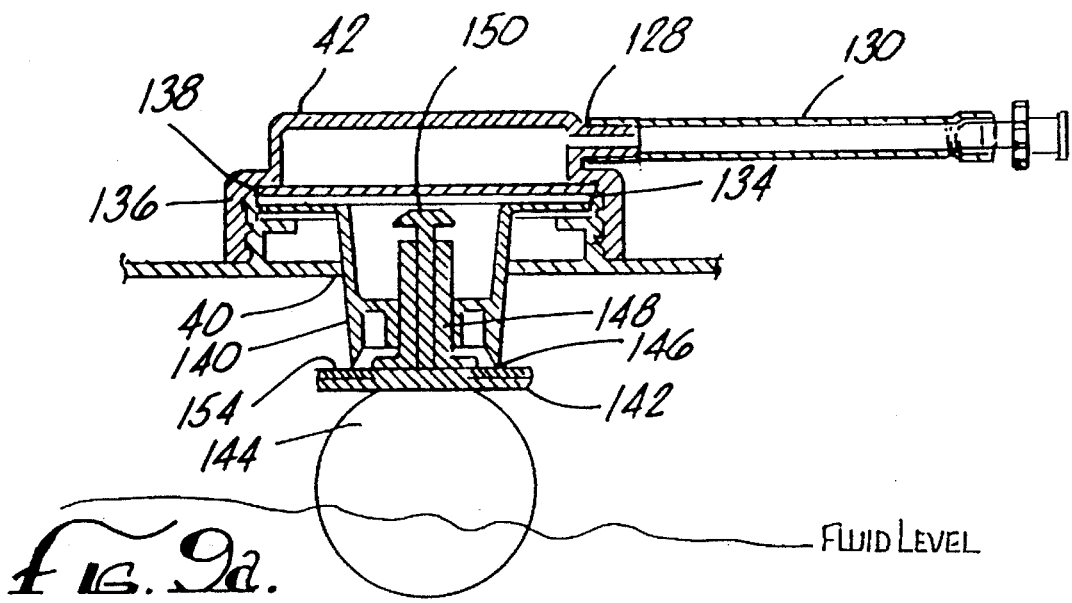
FIG. 9a is an enlarged cross-sectional view of the vacuum port and vacuum connector in the closed position taken along line 4—4 of FIG. 4a with the float valve.
Figure 9B:
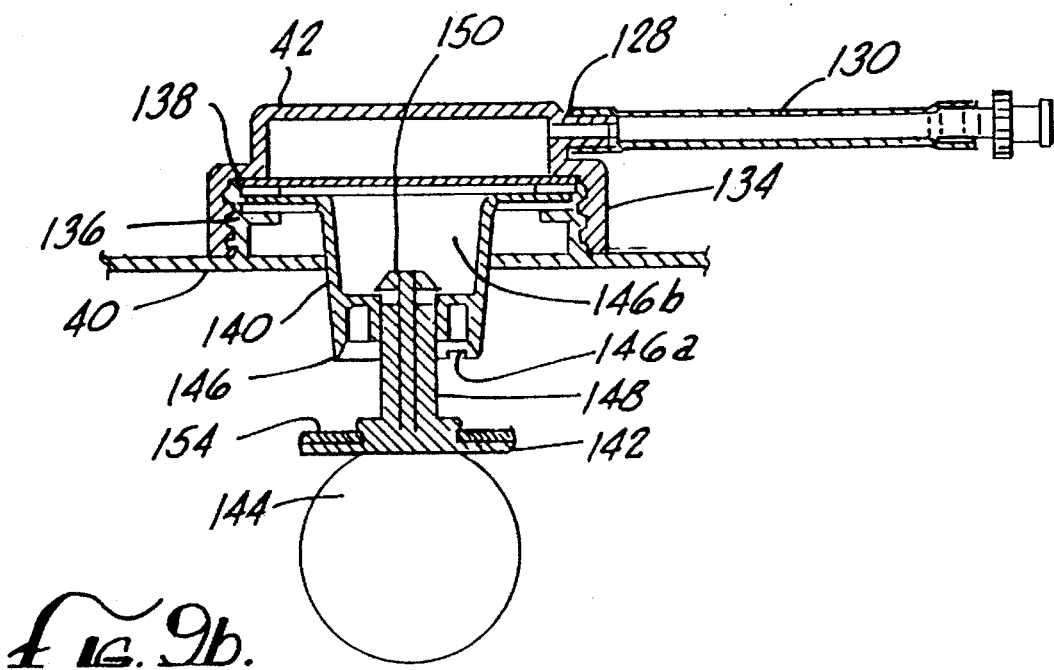

The vacuum port 40, vacuum connector 42, and attached components are shown in FIGS. 9a and 9b. Removably attached to the vacuum port 40 is a vacuum connector 42 which includes a vacuum fitting 128 for connection of the vacuum line 130 which, in turn, is attached to the inlet (vacuum) side 132 of the vacuum pump 14. All components are assembled in a vacuum tight manner. For example, the vacuum connector has a threaded inner surface 134 which mates with matching threads on the outer surface 136 of the vacuum port 40. Attached to the vacuum connector 42, such that air flowing to the vacuum pump must pass therethrough, is a non-wetting filter material 138 with a pore size equal to or less than 0.8 microns desinged to minimize or prevent droplets of liquid bacteria collected in the container 12 from entering the vacuum line. To further prevent collected liquid from entering the vacuum system, a baffle 140 is located between the vacuum port 40 and the vacuum connector 42. Suspended within the baffle 140 is a cut-off valve 142 with a float 144 which is designed as a fail-safe mechanism to prevent fluid from entering the vacuum pump if the container becomes overfilled. FIG. 9a shows the cut-off valve 142 in its closed position; FIG. 9b shows the valve 142 in its open position.

Referring to FIG. 9b, in order for fluid droplets to enter the vacuum line 130, they must flow around the float 144 and the seal edges 146, up along the float stem 148, around the float cap 150 and through the filter 138. The float stem 148 and the float cap 150 have an X-shaped cross section so that, while the droplets see a tortuous path, air can readily flow through the baffled valve assembly.

As shown in FIG. 9a if the container becomes filled with liquid, the rising fluid raises the float 144 and a sealing gasket 154 carried above the float 144 is forced against the seat edge 146, creating a liquid and vacuum seal. This is further aided by the vacuum in the space above the sealing gasket 154 which holds the gasket 154 tightly against the seat edge 146. Seat edge 146 has a notch 146a in it to allow for a controlled leak into the space 146b above gaskt 154. The sizing of notch 146a is such that the vacuum generated by the pump 14 is sufficient to permit the vacuum to rise the approximately 10 inches of mercury at which time a vacuum switch 236, mounted on control module 18 operates to shut off motor 44 and sound an alarm. As the vacuum decreases the motor will restart and the alarm will go off. As the vacuum increases or as the motor current rises above a pre-selected value, the mortor will again be shut off and sound the alarm. This alternating alarm condition will persist until the container is emptied.

The vacuum switch will also operate to shut off the motor and trigger an alarm if any obstruction in the flow path from pad 24 to motor inlet 132 is present causing the vacuum sensed by vacuum switch 236 to rise to approximately 10 inches of mercury. Possible reasons for a rise in vacuum are kinked tubing in the inlet system, blocked or "wet" filter, or reservoir fluid level that raises the float up to seal off flow of air to the filter membrane.

The high vacuum due to kinking or blockages will disappear simply if the kink or blockage is cleared. It is also easily eliminated once the filter is replaced. If the high vacuum is due to the reservoir fluid level causing the float to rise and seal off the filter membrane, the fluid level must be lowered for normal operation to resume. The vacuum can only be reduced by bleeding air into the space above the gasket through the notch 146a in the sealing ring.

This is best accomplished by turning the unit off and draining the reservoir. If the motor is not turned off, the float may not drop and the high vacuum may persist. If it does, the vacuum switch will operate to shut off the pump.

Once all openings to the reservoir are closed and the unit is turned on, and the vacuum dissipates (i.e. drops below 5" Hg), the motor should start and normal operation can proceed. The motor normally will not start at vacuum levels greater than 7.5' Hg and will draw currents in excess of 1 ampere when starting with a high vacuum preload. A current sensing circuit will shut of power to the motor when current above a present value (1 ampere) is sensed. As the vacuum decays, the start-up current required by the motor drops. Power will be supplied to the motor when the start-up current is at the appropriate level.

The current sensing circuitry is designed to protect the motor. It also provides a means to control pump operation.

Pump motor speed can be adjusted to match system vacuum to minimize current draw in order to obtain maximum battery life. During "dry" operation (the patient is not voiding), the pump motor requires a lower current draw than when the patient is voiding. As fluid enters the system (the patient voids), the system vacuum level increases and the increase is sensed by the vacuum switch. The increase can serve as a trigger to increase pump speed to draw the fluid from the patient at the maximum possible rate. As the fluid is withdrawn from the pad and moves through the system, the system vacuum level drops. The decrease in vacuum level, sensed by the vacuum switch can be used as a means to provide a signal to the control circuitry to supply the motor with a lower current level to conserve battery life.

Alternatively, a variable speed motor can be used with the motor speed varying inversely to the vacuum level; i.e. as the vacuum dissipates the motor speeds up increasing the pump suction.

As best shown in FIG. 2 mounted on the outside surface 156 of the control module 18 is a tilt switch 158. The embodiment shown in FIG. 2 includes a conical lower portion 160 which encloses a sensor and a float, ball or a drop of mercury. The sensor responds to the fluid collection system 10 being tilted from the horizontal and the ball, float or mercury being moved from its rest position. The tilting of the system causes the activation of the sensor which, in turn, causes the pump to shut down. Several different tilt switches are commercially available. To reduce the sensitivity of the system to transient tilting which may occur when the unit is moved, the control module 18 is preferably programmed with a time delay which prevents shut down if the tilt switch is quickly returned to its normal resting position.

Figures 10, 11:
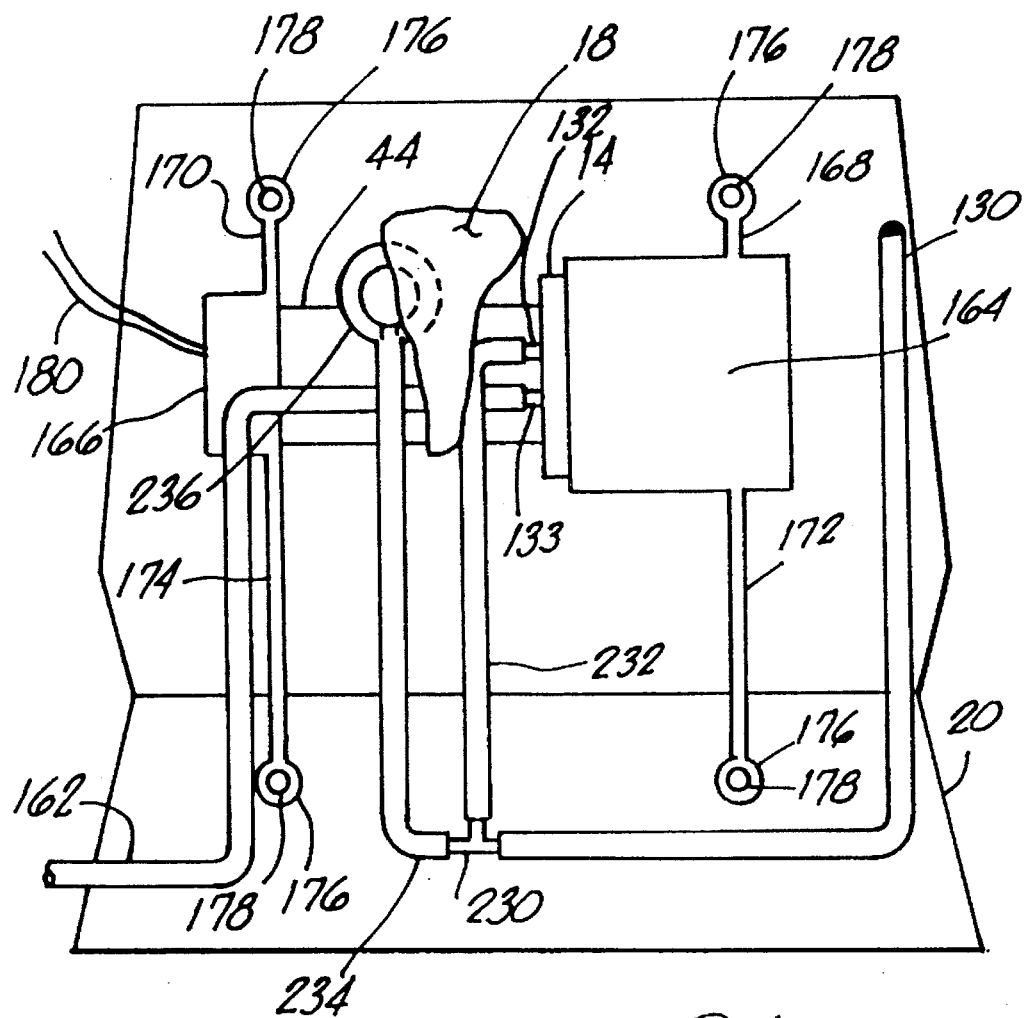
FIG. 10 is an enlarged end view of the pump and motor assembly taken along line 10—10 of FIG. 2.
FIG. 11 is an enlarged cross sectional view of the vacuum pump exhaust muffler.

FIG. 10 is an enlarged drawing showing an end view of the vacuum pump 14 and motor 44. The vacuum line 130 connects the vacuum connector 42 to the inlet (vacuum) side 132 of the vacuum pump 14. Interposed between the vacuum line 130 and the inlet side of 132 of the pump is tee fitting 230 and pump inlet line 232. Attached to tee 230 is vacuum swtich inlet line 234 which connects to vacuum switch 236 mounted to control module. Vacuum swtich 236 therefore is capable of sensing the vacuum from drain tube 22 to motor inlet 132. On the exit side 133 of the vacuum pump 14 is an exhaust line 162 for discharge of the gases removed from container 12, drain tube 22 and the urine collection pad 24. In order to reduce noise and vibration of the fluid collection system 10 caused by the vacuum pump 14 and motor 44, the pump 14 and motor 44 are at least partly enclosed in a flexible elastic polymer or rubber material and suspended in a space within the frame 20 by upper and lower suspenders. The preferred version of the flexible enclosures shown in FIGS. 2 and 10 includes a boot 164 on one end of pump 14 and a separate collar 166 which surrounds a portion of the motor 44. Attached to the boot 164 and collar 166 and fabricated from the same material as the boot 164 and collar 166 are upper pump suspender 168, upper motor suspender 170, lower pump suspender 172 and lower motor suspender 174. Each suspender 168, 170, 172, 174 also has a free end with a loop 176 formed in the free end. The loops are placed onto rods, hooks or set offs 178 mounted to the frame 20. In the embodiment shown, the set offs 178 also serve to hold the control module 18. Since all connections between the pump 14, the motor 44 and the frame 20 are soft and flexible (the other connections are the vacuum line 130 and exhaust line 162, which are flexible tubing, and electrical wires 180) any vibration generated by the pump 14 or motor 44 is isolated from the frame 20. The partial enclosure of the pump 14 and the motor 44 also reduces transmission of sound while exposing a sufficient surface area of the pump and motor for dissipation of heat.

In order to further reduce transmission of noise from the vacuum pump, the exhaust line 162 is attached to a muffler 182 which is in turn attached to a noise and odor absorbing material 48.

An embodiment of the muffler 182 is shown in FIG. 11. The muffler 182 consists of a plastic tube 184, several energy absorbing baffles 186, 188 located along the length of the tube, an inlet conduit 190, an outlet conduit 192, and one or more internal conduits 194. In the embodiment shown in FIG. 11, the tube 184 is formed from a transparent plastic. Four energy absorbing baffles are equally spaced along the tube 184 with one energy absorbing baffle 186 located at each end and the two additional centrally located energy absorbing baffles (the central energy absorbing baffles) 188 located along the tube 184 spaced from each other and from the end energy absorbing baffles 1986. The energy absorbing baffles 186 and 188 are shown to be bell shaped, but this shape is not critical to the proper functioning of the muffler 182. The inlet conduit 190 penetrates one of the end energy absorbing baffles 186 and the two central energy absorbing baffles 190 located within the tube 184. Likewise, the outlet conduit 192 penetrates the other end energy absorbing baffles 186 and the two central energy absorbing baffles 188 within the tube 184. Additionally, there is an opening through, or an internal conduit 194 penetrating each of the central energy absorbing baffles 188. The interface between the conduits 190, 192, 194, and the energy absorbing baffles 186, 188 and between the energy absorbing baffles 186, 188 and the wall of the tube 184 are air tight so gases entering the muffler 182 flow through the desired path described below.

While the tube 184 is preferably formed of a plastic material because of its light weight and sound absorbing characteristics, any tubular material may be used. Likewise, the preferred material for the energy absorbing baffles 186, 188 is an elastomeric polymer such as any of the synthetic rubbers, polyuretheane or TVC. The conduits 190, 192, 194 can be plastic tubing such as polyethylene, polycarbonate, polyurethane.

In use, exhaust gases exiting the vacuum pump and entering the muffler (the arrows in FIG. 11) enter the inlet conduit 190, and flow along its length to be deposited in the outlet chamber 196, pass through a first internal conduit 194 into a central chamber 196 and then through the second internal conduit 190 into the inlet chamber 200 where it enters the outlet conduit 192. The gas then exists the filter end 202 of the outlet tube 192 which is connected to the absorbent 48 and then to the exterior of the system 10. In this manner, a five (5) inch muffler has an effective flow length of about 11.5 inches due to the zig-zag flow path through which the gas passes. Further, each component of the muffler acts to absorb noise generated by the pump or the flowing gas.

A typical odor and noise absorbing material 48 is composed of an open pore depth filter, such as a three dimensional polyurethane, or polyester material, which may also have an absorbent, such as activated carbon bound therein, trapped within the pores or adhered to the surface of the filter. A preferred embodiment is an open pore mat which is about 9"×5" and about 0.5" thick enclosed in a box 204. It is impossible to form the odor and noise absorbing material 48 into a series of subcompartments which combine the noise reduction and odor absorbing function. The pump exhaust gas enters the box 204 at an upper corner 206 and exits from the lower bottom surface of the vent 208 on the lower bottom surface of the box 204. The vent is preferably located as far removed as possible from the upper corner 204.

To use the fluid collection system 10 embodying features of the invention a collection pad 24 is placed on the patient and held in place by straps, under garments or other means commonly used to hold diapers, menstrual pads or the like.

The pad 24 includes a fluid collection tube 23 mounted in or on absorbent material enclosed in the pad 24 and, preferably, a wicking structure (not shown) to aid in feeding fluid deposited on the pad 20 to the fluid collection tube 23. A suitable pad is shown in U.S. Pat. No. 4,747,166 to Kuntz and improvements thereto. However, other means to collect body fluids can be used with the fluid collection system 10. The fluid collection tube 23 in turn is connected to the drain tube 22 which provides a fluid flow path into the container 12.

To assemble and operate the fluid collection system 10, the removable container 12 is placed in the frame 20, the vacuum line 130 is attached to the vacuum port 40, a first end of the drain tube is attached to the outlet valve 26, or if a sampling chamber 28 is used, to the sampling chamber 28 and the second end of the drain tube is attached to the fluid collection tube 23. The container 12 is secured in the frame 20 by attaching the cover 210 to the frame 20.

The motor 44, powered either by a rechargeable battery pack or a detachable wall mounted power supply, which is controlled by the electrical control module, drives the vacuum pump 14. When the pump is operating, the interior of the container 12 is placed under vacuum. That vacuum is, in turn, applied through inlet port 30 and inlet connector 32 to the drain tube 22. As a result, suction is applied to the fluid collection tube 23, continuously drawing fluid from the pad 24 into the container 12.

Although the present invention and the components of the invention have been described in considerable detail with reference to a preferred versions and use thereof, other versions and uses are possible. For example, the vented valve may be used on various different containers holding various different liquids other than urine. Bubbling and foaming of the liquid in the container by using unvented valves can vaporize some of the fluid, cause chemical reactions in oxygen sensitive materials, and result in air bubbles being entrapped in the fluid being dispensed. It is also important to use a vented valve where the contents of the vessel is under pressure. If the liquid is under pressure the liquid will surge out of the valve when opened.

Therefore, the spirit and scope of the appended claims should not be limited to the description of the preferred versions contained herein.

What is claimed is:

1. A fluid collection apparatus for removing liquid from a collection pad attached to a living body, the fluid collection apparatus comprising:

a carrier having a collection vessel removably mounted thereon, a vacuum pump mounted in the carrier, and means for powering the vacuum pump for continuous operation mounted thereto, a) the collection vessel being a container having an internal space for collection of fluid, the collection vessel having
   i) an inlet port in a first upper portion of the collection vessel, said inlet port being sealed by a removable attached inlet connector having a flow channel therethrough, said inlet connector containing a one way valve which prevents fluid in the vessel from passing through the inlet connector, and
   ii) a sealable drainage port located in a surface of the vessel, b) the vacuum pump having an inlet port connected by a tubular conduit to a vacuum port located in a second upper portion of the vessel so that operation of the vacuum pump creates a vacuum characterized as a pressure within the vessel which is less than ambient pressure, and c) a gas pervious but liquid impervious material interposed between the vessel interior and the pump inlet to prevent liquid in the vessel from exiting the vessel through the tubular conduit, the carrier further including a level sensing switch operatively connected to the vacuum pump, the switch functioning to shut off the pump if the vessel is tilted beyond a preset angle from its normal resting orientation, the fluid collection apparatus being operatively connected to a collection pad by a drain tube having a first end attached to the pad and a second end attached to the inlet connector so that the vacuum in the vessel will cause liquid to flow from the pad through the drain tube and be deposited in the vessel.

2. The fluid collection apparatus of claim 1 wherein the carrier further includes a vacuum sensing switch operatively connected to the vacuum pump, the vacuum switch functioning to shut off the pump if the vacuum in the fluid collection system exceeds a preset value and to turn on the pump if the vacuum in the fluid collection system drops below a pre-set value.

3. The fluid collection apparatus of claim 1 further including a control port in a third upper portion of the vessel, said control port being removably sealed by a control connector, the control connector including a liquid level sensing switch, said liquid level sensing switch functioning to suspend operation of the vacuum pump when a predetermined amount of liquid is contained in the vessel.

4. The fluid collection apparatus of claim 1 wherein the pump is at least partially held and surrounded by a boot, the boot having at least two elastic suspenders attached thereto, the suspenders positioning the pump within the carrier without the pump contacting the carrier.

5. The fluid collection apparatus of claim 1 wherein the vacuum pump has an exit side connected to a noise muffler, said noise muffler comprising a tube having an inlet end and an outlet end, first energy absorbing baffles located in the inlet end, second energy absorbing baffles located in the outlet end, and third energy absorbing baffles located within the tubular conduit between the first energy absorbing baffles and the second energy absorbing baffles, a hollow inlet conduit passing through both the first energy absorbing baffles and the third energy absorbing baffles, a hollow outlet conduit passing through both the second energy absorbing baffles and the third energy absorbing baffles and a hollow internal conduit passing through the third energy absorbing baffles such that a gas stream feed into the first hollow conduit at a point exterior to the inlet end of tube will pass serially through the hollow inlet, a first internal portion of the tube, the internal conduit, a second internal portion of the tube, and the exit conduit and exit the outlet end of the tube.

6. The fluid collection apparatus of claim 1 wherein air evacuated from the collection vessel passes through the vacuum pump and is fed through a sound muffler of fixed length to a noise and odor absorbent material, said muffler being divided into chambers by energy absorbing baffles, the air flowing in a non-linear path through the muffler, the length of the path of airflow, through the muffler being greater than the length of the muffler.

7. The fluid collection apparatus of claim 1 wherein the carrier has attached thereto a cover which can be moved from a closed position to an open position to allow removal of the collection vessel, the cover including a locking mechanism to prevent accidental removal of the collection vessel compromising a tab mounted on the frame, said tab extending through an opening in the cover when the cover is in its closed position and a structure substantially enclosed within the cover, the structure having a trigger extending through the cover, a finger which interlocks with an extension attached to the carrier and a raised portion which contacts the tab, said raised portion holding the tab in the opening in the cover while such contact is maintained, such that the cover cannot be moved to its open position unless the finger is withdrawn from its interlocking position with the extension and the raised portion is removed from contact with the tab by depressing the trigger and simultaneously moving the tab from its position within the opening in the frame by applying an external force to the tab.

8. The fluid collection apparatus of claim 1 further having a motor positioned to drive the pump, the motor at least partly surrounded by a collar, the collar having at least two elastic suspenders positioning the motor within the carrier without the motor contacting the carrier.

9. The fluid collection apparatus of claim 1 wherein the vacuum pump is driven by an electric motor and the system further includes a vacuum sensor operatively connected to a control means, the vacuum sensor set to detect the vacuum in the system and send a control signal to the control means such that when the vacuum in the system increases above a preset level, the control module causes an increase in the current being delivered to the motor and when the vacuum in the system decreases below a preset level the control module causes a decrease in the current being delivered to the motor.

10. The fluid collection apparatus of claim 1 wherein the gas pervious but liquid impervious material is a non-wettable filter medium held in the vacuum port above the vessel interior, said vacuum port further including a float having means cooperating therewith to interrupt the imposition of vacuum on the vessel interior if the amount of liquid exceeds a predetermined quantity.

11. The fluid collection apparatus of claims 10 wherein the liquid impervious material has a pore size less than about 0.8 microns.

12. The fluid collection apparatus of claim 10 wherein said vacuum port includes a tubular portion depending therefrom to direct air evacuated from the vessel through the filter media, said tubular portion also functioning as a baffle to prevent direct liquid contact with the filter medium, said tubular portion has a lower edge and when liquid in the chamber exceeds a desired level the float moves the gasket into sealing contact with the lower edge of the tubular portion, interrupting the flow of any of the contents of the vessel through the vacuum port.

13. The fluid collection apparatus of claim 1 wherein the sealable drainage port includes a vented drain valve which allows ambient air to pass through the valve to a liquid free space within the collection vessel, the ambient air passing counter-current to fluid exiting through the valve without contacting said exiting fluid.

14. The fluid collection apparatus of claim 13 wherein the vented drain valve comprises a shell having a wall surrounding a lumen extending therethrough, a piston located within and slidable along at least a portion of the lumen in the shell and a hollow spout depending from the shell wherein,
the lumen in the shell extends from a first end of the shell to a second end of the shell, the lumen having a uniform cross-section along its length,
the piston located in the lumen in the shell has cross-sectional dimensions smaller than the dimensions of the cross-section of the lumen in the shell, and
at least a first and a second seal are located between the piston and the shell, the seals being spaced apart such that a fluid will not pass along the length of the piston between the piston and the shell, the shell wall having a drain opening at a point between the first end of the shell and the second end of the shell, the opening connecting the shell lumen to the hollow through the spout, the piston having a wall surrounding a passage, the passage extending from an interior end of the piston to a channel piercing the wall of the piston at a point spaced from the interior end of the piston, the first seal circumferentially encircling the piston at a point near the interior end of the piston, and the second seal circumferentially encircling the piston at a point located between the interior end of the piston and the channel through the wall of the piston, such that the first seal and the second seal are both in sealing contact between the piston and the wall of the shell, a hollow tube having a lumen extending therethrough, a first end of the tube being attached to the interior end of the piston so that the lumen of the tube is coextensive with the passage in the piston and extends into the liquid free space within the collection vessel, the seals being located such that when the piston is located within the shell in a first position the first seal is located on a first side of the drain opening through the wall of the shell and the second seal is located on a second side of the drain opening through the wall of the shell, and when the piston is located in the shell in a second position, the second seal is located on the second side of the drain opening, but the entire drain opening is no longer located between the first seal and the second seal.

15. The fluid collection apparatus of claim 14 further including a third seal located between the piston and the shell such that when the piston is in the first position, the third seal is in sealing contact with the shell wall and the channel is isolated from the air surrounding the valve and when the piston is in the second position the third seal no longer isolates the channel from the air surrounding the valve.

16. The fluid collection apparatus of claim 14 wherein the first seal and second seal encircling the piston are formed as an integral part of the piston.

17. The fluid collection apparatus of claim 14 wherein the first seal and second seal are rings of a sealing material interposed between the shell and the piston.

18. The fluid collection apparatus of claim 17 further having a motor positioned to drive the pump, the motor at least partly surrounded by a collar, the collar having at least two elastic suspenders positioning the motor within the frame without the motor contacting the frame.

* * * * *